(12) United States Patent
Gyrn (10) Patent No.: US 9,724,127 B2
(45) Date of Patent: Aug. 8, 2017

(54) INSERTION SYSTEM AND INSERTION KIT (75) Inventor: Steffen Gyrn, Ringsted (DK)

(73) Assignee: Unomedical A/S, Birkeroed (DK)

( * ) Notice: Subject to any disclaimer, the term of this patent is extended or adjusted under 35 U.S.C. 154(b) by 1103 days.

(21) Appl. No.: 13/823,244

(22) PCT Filed: Sep. 23, 2011

(86) PCT No.: PCT/EP2011/066607
§ 371 (c)(1),
(2), (4) Date: May 20, 2013

(87) PCT Pub. No.: WO2012/041784
PCT Pub. Date: Apr. 5, 2012

(65) Prior Publication Data
US 2013/0237918 A1 Sep. 12, 2013

Related U.S. Application Data (60) Provisional application No. 61/386,705, filed on Sep. 27, 2010.

(30) Foreign Application Priority Data

Sep. 27, 2010 (EP) .................................. 10179976

(51) Int. Cl.
A61B 17/34 (2006.01)
A61M 5/158 (2006.01)

(52) U.S. Cl.
CPC .......... A61B 17/3468 (2013.01); A61M 5/158 (2013.01); A61M 2005/1581 (2013.01); A61M 2005/1585 (2013.01); A61M 2209/04 (2013.01)

(58) Field of Classification Search
CPC .......... A61M 5/158; A61M 2005/1581; A61M 2005/1585; A61M 2209/04; A61M 17/3468; A61M 25/0606; A61B 17/3468
See application file for complete search history.

(56) References Cited

U.S. PATENT DOCUMENTS 1,592,462 A 7/1926 MacGregor
2,047,010 A 7/1936 Dickinson
(Continued)

FOREIGN PATENT DOCUMENTS

DE 4 342 329 A1 6/1994
DE 196 31 921 A1 3/1997
(Continued)

OTHER PUBLICATIONS

International Search Report completed Feb. 23, 2012 for International Application No. PCT/EP2011/066607.
(Continued)

Primary Examiner — Theodore Stigell
(74) Attorney, Agent, or Firm — Wilson Sonsini Goodrich & Rosati (57) ABSTRACT Insertion System (2) and an Insertion kit is disclosed, the Insertion System comprising a housing (4) with a wall (6) defining a cavity (8), an actuator element (10), a first part (12) and a second part (14), the first part comprising a subcutaneous element (16) and a first base element (18) with at least one base plate engagement element (20), the second part comprising a needle hub (22) and at least one Insertion needle (24) secured to the needle hub with the second part movably arranged from a first position to a second position relative to the housing along an Insertion axis (X), wherein the housing comprises at least one first coupling element (28) for releasably securing the Insertion System to an inserter device, and wherein the actuator element comprises an outer part (32) external to the housing such that manual actuation of the actuator element in relation to the housing is enabled.

27 Claims, 7 Drawing Sheets (56) References Cited

U.S. PATENT DOCUMENTS

| | | |
|---|---|---|
| 2,295,849 A | 9/1942 | Kayden |
| 2,690,529 A | 9/1954 | Lindblad |
| 2,972,779 A | 2/1961 | Cowley |
| 3,059,802 A | 10/1962 | Mitchell |
| 3,074,541 A | 1/1963 | Roehr |
| 3,149,186 A | 9/1964 | Coanda |
| 3,221,739 A | 12/1965 | Rosenthal |
| 3,221,740 A | 12/1965 | Rosenthal |
| 3,306,291 A | 2/1967 | Burke |
| 3,485,352 A | 12/1969 | Pilger |
| 3,509,879 A | 5/1970 | Bathish et al. |
| 3,519,158 A | 7/1970 | Anderson |
| 3,547,119 A | 12/1970 | Hall et al. |
| 3,575,337 A | 4/1971 | Bernhardt |
| 3,610,240 A | 10/1971 | Harautuneian |
| 3,615,039 A | 10/1971 | Ward |
| 3,670,727 A | 6/1972 | Reiterman |
| 3,783,895 A | 1/1974 | Weichselbaum |
| 3,788,374 A | 1/1974 | Saijo |
| 3,810,469 A | 5/1974 | Hurschman |
| 3,835,862 A | 9/1974 | Villari |
| 3,840,011 A | 10/1974 | Wright |
| 3,893,448 A | 7/1975 | Brantigan |
| 3,937,219 A | 2/1976 | Karakashian |
| 3,986,507 A | 10/1976 | Watt |
| 3,986,508 A | 10/1976 | Barrington |
| 3,995,518 A | 12/1976 | Spiroff |
| 4,022,205 A | 5/1977 | Tenczar |
| 4,188,950 A | 2/1980 | Wardlaw |
| 4,201,406 A | 5/1980 | Dennehey et al. |
| 4,227,528 A | 10/1980 | Wardlaw |
| 4,259,276 A | 3/1981 | Rawlings |
| 4,267,836 A | 5/1981 | Whitney et al. |
| 4,296,786 A | 10/1981 | Brignola |
| 4,315,505 A | 2/1982 | Crandall et al. |
| 4,333,455 A | 6/1982 | Bodicky |
| 4,334,551 A | 6/1982 | Pfister |
| D267,199 S | 12/1982 | Koenig |
| 4,378,015 A | 3/1983 | Wardlaw |
| 4,402,407 A | 9/1983 | Maly |
| 4,415,393 A | 11/1983 | Grimes |
| 4,417,886 A | 11/1983 | Frankhouser et al. |
| 4,464,178 A | 8/1984 | Dalton |
| 4,473,369 A | 9/1984 | Lueders et al. |
| 4,484,910 A | 11/1984 | Sarnoff et al. |
| 4,500,312 A | 2/1985 | McFarlane |
| 4,508,367 A | 4/1985 | Oreopoulos et al. |
| 4,525,157 A | 6/1985 | Vaillancourt |
| 4,530,695 A | 7/1985 | Phillips et al. |
| 4,531,937 A | 7/1985 | Yates |
| 4,543,088 A | 9/1985 | Bootman et al. |
| 4,563,177 A | 1/1986 | Kamen |
| 4,610,469 A | 9/1986 | Wolff-Mooij |
| 4,617,019 A | 10/1986 | Fecht |
| 4,713,059 A | 12/1987 | Bickelhaupt et al. |
| 4,734,092 A | 3/1988 | Millerd |
| 4,755,173 A | 7/1988 | Konopka et al. |
| 4,817,603 A | 4/1989 | Turner et al. |
| RE32,922 E | 5/1989 | Levin et al. |
| 4,838,871 A | 6/1989 | Luther |
| 4,840,613 A | 6/1989 | Balbierz |
| 4,850,974 A | 7/1989 | Bickelhaupt et al. |
| 4,850,996 A | 7/1989 | Cree |
| 4,863,016 A | 9/1989 | Fong et al. |
| 4,878,897 A | 11/1989 | Katzin |
| 4,890,608 A | 1/1990 | Steer |
| 4,894,054 A | 1/1990 | Miskinyar |
| 4,895,570 A | 1/1990 | Larkin |
| 4,917,669 A | 4/1990 | Bonaldo |
| 4,935,010 A | 6/1990 | Cox et al. |
| 4,950,163 A | 8/1990 | Zimble |
| 4,950,252 A | 8/1990 | Luther et al. |
| 4,956,989 A | 9/1990 | Nakajima |
| 4,970,954 A | 11/1990 | Weir et al. |
| 4,978,338 A | 12/1990 | Melsky et al. |
| 4,982,842 A | 1/1991 | Hollister |
| 4,986,817 A | 1/1991 | Code |
| 4,994,042 A | 2/1991 | Vadher |
| 4,994,045 A | 2/1991 | Ranford |
| 5,011,475 A | 4/1991 | Olson |
| 5,020,665 A | 6/1991 | Bruno |
| 5,024,662 A | 6/1991 | Menes et al. |
| 5,067,496 A | 11/1991 | Eisele |
| 5,092,853 A | 3/1992 | Couvertier, II |
| 5,098,389 A | 3/1992 | Cappucci |
| 5,112,313 A | 5/1992 | Sallee |
| 5,116,319 A | 5/1992 | Van den Haak |
| 5,116,325 A | 5/1992 | Paterson |
| 5,121,751 A | 6/1992 | Panalletta |
| 5,129,884 A | 7/1992 | Dysarz |
| 5,135,502 A | 8/1992 | Koenig, Jr. et al. |
| 5,137,516 A | 8/1992 | Rand et al. |
| 5,137,524 A | 8/1992 | Lynn et al. |
| 5,141,496 A | 8/1992 | Dalto et al. |
| 5,147,375 A | 9/1992 | Sullivan et al. |
| 5,163,915 A | 11/1992 | Holleron |
| 5,172,808 A | 12/1992 | Bruno |
| 5,176,643 A | 1/1993 | Kramer et al. |
| 5,176,650 A | 1/1993 | Haining |
| 5,176,662 A | 1/1993 | Bartholomew et al. |
| 5,186,712 A | 2/1993 | Kelso et al. |
| 5,188,611 A | 2/1993 | Orgain |
| RE34,223 E | 4/1993 | Bonaldo |
| 5,205,820 A | 4/1993 | Kriesel |
| 5,222,947 A | 6/1993 | D'Amico |
| 5,232,454 A | 8/1993 | Hollister |
| 5,248,301 A | 9/1993 | Koenig et al. |
| 5,256,149 A | 10/1993 | Banik et al. |
| 5,256,152 A | 10/1993 | Marks |
| 5,257,980 A | 11/1993 | Van Antwerp et al. |
| 5,267,963 A | 12/1993 | Bachynsky |
| 5,269,799 A | 12/1993 | Daniel |
| 5,271,744 A | 12/1993 | Kramer et al. |
| 5,279,579 A | 1/1994 | D'Amico |
| 5,279,591 A | 1/1994 | Simon |
| 5,282,793 A | 2/1994 | Larson |
| 5,300,030 A | 4/1994 | Crossman et al. |
| 5,312,359 A | 5/1994 | Wallace |
| 5,312,369 A | 5/1994 | Arcusin et al. |
| 5,316,246 A | 5/1994 | Scott et al. |
| 5,324,302 A | 6/1994 | Crouse |
| 5,342,319 A | 8/1994 | Watson et al. |
| 5,342,324 A | 8/1994 | Tucker |
| 5,344,007 A | 9/1994 | Nakamura et al. |
| 5,350,392 A | 9/1994 | Purcell et al. |
| 5,354,280 A | 10/1994 | Haber et al. |
| 5,354,337 A | 10/1994 | Hoy |
| 5,366,469 A | 11/1994 | Steg et al. |
| 5,372,592 A | 12/1994 | Gambale |
| 5,372,787 A | 12/1994 | Ritter |
| 5,376,082 A | 12/1994 | Phelps |
| 5,379,895 A | 1/1995 | Foslien |
| 5,384,174 A | 1/1995 | Ward et al. |
| 5,387,197 A | 2/1995 | Smith et al. |
| 5,390,669 A | 2/1995 | Stuart et al. |
| 5,391,151 A | 2/1995 | Wilmot |
| 5,403,288 A | 4/1995 | Stanners |
| 5,405,332 A | 4/1995 | Opalek |
| 5,425,715 A | 6/1995 | Dalling et al. |
| 5,429,607 A | 7/1995 | McPhee |
| 5,429,613 A | 7/1995 | D'Amico |
| 5,439,473 A | 8/1995 | Jorgensen |
| D362,718 S | 9/1995 | Deily et al. |
| 5,449,349 A | 9/1995 | Sallee et al. |
| 5,451,210 A | 9/1995 | Kramer et al. |
| 5,478,316 A | 12/1995 | Bitdinger et al. |
| 5,490,841 A | 2/1996 | Landis |
| 5,501,675 A | 3/1996 | Erskine |
| 5,505,709 A | 4/1996 | Funderburk et al. |
| 5,507,730 A | 4/1996 | Haber et al. |
| 5,514,117 A | 5/1996 | Lynn |
| 5,520,654 A | 5/1996 | Wahlberg |
| 5,522,803 A | 6/1996 | Teisson-Simony |
| 5,527,287 A | 6/1996 | Miskinyar et al. |

(56) References Cited

U.S. PATENT DOCUMENTS

| | | |
|---|---|---|
| 5,533,974 A | 7/1996 | Gaba |
| 5,540,709 A | 7/1996 | Ramel |
| 5,545,143 A | 8/1996 | Fischell |
| 5,545,152 A | 8/1996 | Funderburk et al. |
| 5,549,577 A | 8/1996 | Siegel et al. |
| 5,554,130 A | 9/1996 | McDonald et al. |
| 5,558,650 A | 9/1996 | McPhee |
| 5,562,629 A | 10/1996 | Haughton et al. |
| 5,562,636 A | 10/1996 | Utterberg |
| 5,573,510 A | 11/1996 | Isaacson |
| 5,575,777 A | 11/1996 | Cover et al. |
| 5,584,813 A | 12/1996 | Livingston et al. |
| 5,586,553 A | 12/1996 | Halili |
| 5,591,188 A | 1/1997 | Waisman |
| 5,599,309 A | 2/1997 | Marshall et al. |
| 5,599,315 A | 2/1997 | McPhee |
| 5,599,318 A | 2/1997 | Sweeney et al. |
| 5,628,765 A | 5/1997 | Morita |
| 5,643,214 A | 7/1997 | Marshall |
| 5,643,216 A | 7/1997 | White |
| 5,643,220 A | 7/1997 | Cosme |
| 5,658,256 A | 8/1997 | Shields |
| 5,662,617 A | 9/1997 | Odell et al. |
| 5,665,071 A | 9/1997 | Wyrick |
| 5,665,075 A | 9/1997 | Gyure et al. |
| 5,676,156 A | 10/1997 | Yoon |
| 5,681,323 A | 10/1997 | Arick |
| 5,695,476 A | 12/1997 | Harris |
| 5,697,907 A | 12/1997 | Gaba |
| 5,700,250 A | 12/1997 | Erskine |
| 5,702,371 A | 12/1997 | Bierman |
| 5,704,920 A | 1/1998 | Gyure |
| 5,709,662 A | 1/1998 | Olive et al. |
| 5,714,225 A | 2/1998 | Hansen et al. |
| 5,738,641 A | 4/1998 | Watson et al. |
| 5,741,288 A | 4/1998 | Rife |
| 5,752,923 A | 5/1998 | Terwilliger |
| 5,807,316 A | 9/1998 | Teeple |
| 5,807,348 A | 9/1998 | Zinger et al. |
| 5,810,835 A | 9/1998 | Ryan et al. |
| 5,817,058 A | 10/1998 | Shaw |
| 5,820,598 A | 10/1998 | Gazza et al. |
| 5,827,236 A | 10/1998 | Takahashi |
| 5,833,666 A | 11/1998 | Davis et al. |
| 5,843,001 A | 12/1998 | Goldenberg |
| 5,848,990 A | 12/1998 | Cirelli et al. |
| 5,851,197 A | 12/1998 | Marano et al. |
| 5,858,001 A | 1/1999 | Tsals et al. |
| 5,865,806 A | 2/1999 | Howell |
| 5,899,886 A | 5/1999 | Cosme |
| 5,911,705 A | 6/1999 | Howell |
| 5,913,846 A | 6/1999 | Szabo |
| 5,916,199 A | 6/1999 | Miles |
| 5,919,167 A | 7/1999 | Mulhauser et al. |
| 5,919,170 A | 7/1999 | Woessner |
| 5,925,032 A | 7/1999 | Clements |
| 5,935,109 A | 8/1999 | Donnan |
| 5,947,931 A | 9/1999 | Bierman |
| 5,947,935 A | 9/1999 | Rhinehart et al. |
| 5,951,523 A | 9/1999 | Osterlind et al. |
| 5,954,643 A | 9/1999 | VanAntwerp et al. |
| 5,957,892 A | 9/1999 | Thorne |
| 5,957,897 A | 9/1999 | Jeffrey |
| 5,968,011 A | 10/1999 | Larsen et al. |
| 5,971,966 A | 10/1999 | Lav |
| 5,975,120 A | 11/1999 | Novosel |
| 5,980,488 A | 11/1999 | Thorne |
| 5,980,506 A | 11/1999 | Mathiasen |
| 5,984,224 A | 11/1999 | Yang |
| 5,984,897 A | 11/1999 | Peterson et al. |
| D417,733 S | 12/1999 | Howell et al. |
| 6,017,328 A | 1/2000 | Fischell et al. |
| 6,017,598 A | 1/2000 | Kreischer et al. |
| D421,119 S | 2/2000 | Musgrave et al. |
| 6,024,727 A | 2/2000 | Thorne et al. |
| 6,039,629 A | 3/2000 | Mitchell |
| 6,042,570 A | 3/2000 | Bell et al. |
| 6,045,533 A | 4/2000 | Kriesel et al. |
| 6,045,534 A | 4/2000 | Jacobsen et al. |
| 6,050,976 A | 4/2000 | Thorne et al. |
| 6,053,893 A | 4/2000 | Bucher |
| 6,053,930 A | 4/2000 | Ruppert |
| 6,056,718 A | 5/2000 | Funderburk et al. |
| 6,056,726 A | 5/2000 | Isaacson |
| 6,074,369 A | 6/2000 | Sage et al. |
| 6,074,371 A | 6/2000 | Fischell |
| 6,077,244 A | 6/2000 | Botich et al. |
| 6,079,432 A | 6/2000 | Paradis |
| 6,086,008 A | 7/2000 | Gray et al. |
| 6,086,575 A | 7/2000 | Mejslov |
| 6,090,068 A | 7/2000 | Chanut |
| 6,093,172 A | 7/2000 | Funderburk et al. |
| 6,093,179 A | 7/2000 | O'Hara et al. |
| 6,099,503 A | 8/2000 | Stardella |
| 6,105,218 A | 8/2000 | Reekie |
| 6,106,498 A | 8/2000 | Friedli et al. |
| 6,120,482 A | 9/2000 | Szabo |
| 6,123,690 A | 9/2000 | Mejslov |
| 6,132,755 A | 10/2000 | Eicher et al. |
| 6,139,534 A | 10/2000 | Niedospial, Jr. |
| 6,159,181 A | 12/2000 | Crossman et al. |
| 6,183,464 B1 | 2/2001 | Sharp et al. |
| 6,191,338 B1 | 2/2001 | Haller |
| 6,193,694 B1 | 2/2001 | Bell et al. |
| 6,210,420 B1 | 4/2001 | Mauze et al. |
| 6,219,574 B1 | 4/2001 | Cormier et al. |
| 6,221,058 B1 | 4/2001 | Kao et al. |
| 6,248,093 B1 | 6/2001 | Moberg |
| 6,261,272 B1 | 7/2001 | Gross et al. |
| 6,293,925 B1 | 9/2001 | Safabash et al. |
| 6,302,866 B1 | 10/2001 | Marggi |
| 6,319,232 B1 | 11/2001 | Kashmer |
| 6,322,535 B1 | 11/2001 | Hitchins et al. |
| 6,322,808 B1 | 11/2001 | Trautman et al. |
| 6,334,856 B1 | 1/2002 | Allen et al. |
| 6,355,021 B1 | 3/2002 | Nielsen et al. |
| 6,364,113 B1 | 4/2002 | Faasse et al. |
| 6,378,218 B2 | 4/2002 | Sigwart et al. |
| 6,379,335 B1 | 4/2002 | Rigon et al. |
| 6,387,076 B1 | 5/2002 | Van Lunduyt |
| 6,387,078 B1 | 5/2002 | Gillespie, III |
| 6,405,876 B1 | 6/2002 | Seshimoto et al. |
| 6,440,096 B1 | 8/2002 | Lastovich et al. |
| 6,447,482 B1 | 9/2002 | Rønborg et al. |
| 6,450,992 B1 | 9/2002 | Cassidy, Jr. |
| 6,485,461 B1 | 11/2002 | Mason et al. |
| 6,488,663 B1 | 12/2002 | Steg |
| 6,503,222 B2 | 1/2003 | Lo |
| 6,517,517 B1 | 2/2003 | Farrugia et al. |
| 6,520,938 B1 | 2/2003 | Funderburk et al. |
| D472,316 S | 3/2003 | Douglas et al. |
| D472,630 S | 4/2003 | Douglas et al. |
| 6,572,586 B1 | 6/2003 | Wojcik |
| 6,579,267 B2 | 6/2003 | Lynch et al. |
| 6,582,397 B2 | 6/2003 | Alesi et al. |
| 6,595,962 B1 | 7/2003 | Perthu |
| 6,607,509 B2 | 8/2003 | Bobroff et al. |
| 6,607,511 B2 | 8/2003 | Halseth et al. |
| 6,613,064 B2 | 9/2003 | Rutynowski et al. |
| 6,620,133 B1 | 9/2003 | Steck |
| 6,620,136 B1 | 9/2003 | Pressly, Sr. et al. |
| 6,620,140 B1 | 9/2003 | Metzger |
| 6,629,949 B1 | 10/2003 | Douglas |
| 6,645,181 B1 | 11/2003 | Lavi et al. |
| 6,645,182 B1 | 11/2003 | Szabo |
| 6,659,982 B2 | 12/2003 | Douglas et al. |
| 6,685,674 B2 | 2/2004 | Douglas et al. |
| 6,699,218 B2 | 3/2004 | Flaherty et al. |
| 6,702,779 B2 | 3/2004 | Connelly et al. |
| 6,726,649 B2 | 4/2004 | Swenson et al. |
| 6,736,797 B1 | 5/2004 | Larsen et al. |
| 6,743,203 B1 | 6/2004 | Pickhard |
| 6,749,587 B2 | 6/2004 | Flaherty |
| 6,749,589 B1 | 6/2004 | Douglas et al. |

(56) References Cited

U.S. PATENT DOCUMENTS

| | | |
|---|---|---|
| 6,755,805 B1 | 6/2004 | Reid |
| 6,776,775 B1 | 8/2004 | Mohammad |
| 6,790,199 B1 | 9/2004 | Gianakos |
| 6,805,686 B1 | 10/2004 | Fathallah et al. |
| 6,808,506 B2 | 10/2004 | Lastovich et al. |
| 6,811,545 B2 | 11/2004 | Vaillancourt |
| 6,814,720 B2 | 11/2004 | Olsen et al. |
| 6,824,530 B2 | 11/2004 | Wagner et al. |
| 6,824,531 B1 | 11/2004 | Zecha, Jr. et al. |
| 6,830,562 B2 | 12/2004 | Mogensen et al. |
| 6,837,877 B2 | 1/2005 | Zurcher |
| 6,837,878 B2 | 1/2005 | Smutney et al. |
| 6,840,922 B2 | 1/2005 | Nielsen et al. |
| 6,880,701 B2 | 4/2005 | Bergeron et al. |
| 6,923,791 B2 | 8/2005 | Douglas |
| 6,926,694 B2 | 8/2005 | Marano-Ford et al. |
| 6,939,324 B2 | 9/2005 | Gonnelli et al. |
| 6,939,331 B2 | 9/2005 | Ohshima |
| 6,949,084 B2 | 9/2005 | Marggi et al. |
| 6,959,812 B2 | 11/2005 | Reif et al. |
| 6,960,193 B2 | 11/2005 | Rosenberg |
| 6,979,316 B1 | 12/2005 | Rubin et al. |
| 6,991,619 B2 | 1/2006 | Marano-Ford et al. |
| 6,991,620 B2 | 1/2006 | Marano-Ford et al. |
| 6,994,213 B2 | 2/2006 | Giard et al. |
| 6,997,907 B2 | 2/2006 | Safabash et al. |
| 7,014,625 B2 | 3/2006 | Bengtsson |
| 7,018,344 B2 | 3/2006 | Bressler et al. |
| 7,022,108 B2 | 4/2006 | Marano-Ford et al. |
| 7,047,070 B2 | 5/2006 | Wilkinson et al. |
| 7,052,483 B2 | 5/2006 | Wojcik |
| 7,055,713 B2 | 6/2006 | Rea et al. |
| 7,056,302 B2 | 6/2006 | Douglas |
| 7,070,580 B2 | 7/2006 | Nielsen |
| 7,074,208 B2 | 7/2006 | Pajunk et al. |
| D526,409 S | 8/2006 | Nielsen et al. |
| 7,083,592 B2 | 8/2006 | Lastovich et al. |
| 7,083,597 B2 | 8/2006 | Lynch et al. |
| 7,097,631 B2 | 8/2006 | Trautman et al. |
| 7,109,878 B2 | 9/2006 | Mann et al. |
| 7,115,108 B2 | 10/2006 | Wilkenson et al. |
| 7,115,112 B2 | 10/2006 | Mogensen et al. |
| 7,137,968 B1 | 11/2006 | Burrell et al. |
| 7,141,023 B2 | 11/2006 | Diermann et al. |
| 7,147,623 B2 | 12/2006 | Mathiasen |
| 7,186,236 B2 | 3/2007 | Gibson et al. |
| 7,211,068 B2 | 5/2007 | Douglas |
| 7,214,207 B2 | 5/2007 | Lynch et al. |
| 7,214,215 B2 | 5/2007 | Heinzerling et al. |
| 7,250,037 B2 | 7/2007 | Shermer et al. |
| 7,258,680 B2 | 8/2007 | Mogensen et al. |
| D554,253 S | 10/2007 | Kornerup |
| 7,303,543 B1 | 12/2007 | Maule et al. |
| 7,309,326 B2 | 12/2007 | Fangrow, Jr. |
| 7,322,473 B2 | 1/2008 | Fux |
| 7,407,491 B2 | 8/2008 | Fangrow, Jr. |
| 7,407,493 B2 | 8/2008 | Cane' |
| 7,431,876 B2 | 10/2008 | Mejlhede et al. |
| 7,441,655 B1 | 10/2008 | Hoftman |
| 7,569,262 B2 | 8/2009 | Szabo et al. |
| 7,648,494 B2 | 1/2010 | Kornerup et al. |
| 7,766,867 B2 | 8/2010 | Lynch et al. |
| 7,846,132 B2 | 12/2010 | Gravesen et al. |
| 7,850,652 B2 | 12/2010 | Liniger et al. |
| 8,012,126 B2 | 9/2011 | Tipsmark et al. |
| 8,087,333 B2 | 1/2012 | Oishi |
| 8,123,724 B2 | 2/2012 | Gillespie, III |
| 8,303,549 B2 | 11/2012 | Mejlhede et al. |
| 8,323,250 B2 | 12/2012 | Chong et al. |
| 2001/0004970 A1 | 6/2001 | Hollister et al. |
| 2001/0016714 A1 | 8/2001 | Bell et al. |
| 2001/0021827 A1 | 9/2001 | Ferguson et al. |
| 2001/0039387 A1 | 11/2001 | Rutynowski et al. |
| 2001/0039401 A1 | 11/2001 | Ferguson et al. |
| 2001/0041875 A1 | 11/2001 | Higuchi et al. |
| 2001/0049496 A1 | 12/2001 | Kirchhofer |
| 2001/0053889 A1 | 12/2001 | Marggi |
| 2001/0056284 A1 | 12/2001 | Purcell et al. |
| 2002/0022798 A1 | 2/2002 | Connelly et al. |
| 2002/0022855 A1 | 2/2002 | Bobroff et al. |
| 2002/0026152 A1 | 2/2002 | Bierman |
| 2002/0055711 A1 | 5/2002 | Lavi et al. |
| 2002/0068904 A1 | 6/2002 | Bierman et al. |
| 2002/0072720 A1 | 6/2002 | Hague et al. |
| 2002/0074345 A1 | 6/2002 | Schneider et al. |
| 2002/0077599 A1 | 6/2002 | Wojcik |
| 2002/0082543 A1 | 6/2002 | Park et al. |
| 2002/0095138 A1 | 7/2002 | Lynch et al. |
| 2002/0107489 A1 | 8/2002 | Lee |
| 2002/0111581 A1 | 8/2002 | Sasso |
| 2002/0156424 A1 | 10/2002 | Suzuki et al. |
| 2002/0156427 A1 | 10/2002 | Suzuki et al. |
| 2002/0161322 A1 | 10/2002 | Utterberg et al. |
| 2002/0161332 A1 | 10/2002 | Ramey |
| 2002/0161386 A1 | 10/2002 | Halseth et al. |
| 2002/0165493 A1 | 11/2002 | Bierman |
| 2002/0169419 A1 | 11/2002 | Steg |
| 2002/0173748 A1 | 11/2002 | McConnell et al. |
| 2002/0173769 A1 | 11/2002 | Gray et al. |
| 2002/0183688 A1 | 12/2002 | Lastovich et al. |
| 2002/0189688 A1 | 12/2002 | Roorda |
| 2002/0193737 A1 | 12/2002 | Popovsky |
| 2002/0193744 A1 | 12/2002 | Alesi et al. |
| 2003/0014018 A1 | 1/2003 | Giambattista et al. |
| 2003/0060781 A1 | 3/2003 | Mogensen et al. |
| 2003/0069548 A1 | 4/2003 | Connelly et al. |
| 2003/0088238 A1 | 5/2003 | Poulsen et al. |
| 2003/0105430 A1 | 6/2003 | Lavi et al. |
| 2003/0109829 A1 | 6/2003 | Mogensen et al. |
| 2003/0125669 A1 | 7/2003 | Safabash et al. |
| 2003/0125678 A1 | 7/2003 | Swenson et al. |
| 2003/0130619 A1 | 7/2003 | Safabash et al. |
| 2003/0139704 A1 | 7/2003 | Lin |
| 2003/0158520 A1 | 8/2003 | Safabash et al. |
| 2003/0176843 A1 | 9/2003 | Wilkinson |
| 2003/0176852 A1 | 9/2003 | Lynch et al. |
| 2003/0181863 A1 | 9/2003 | Ackley et al. |
| 2003/0181868 A1 | 9/2003 | Swenson |
| 2003/0181873 A1 | 9/2003 | Swenson |
| 2003/0181874 A1 | 9/2003 | Bressler et al. |
| 2003/0187394 A1 | 10/2003 | Wilkinson et al. |
| 2003/0187395 A1 | 10/2003 | Gabel |
| 2003/0199823 A1 | 10/2003 | Bobroff et al. |
| 2003/0216686 A1 | 11/2003 | Lynch et al. |
| 2003/0220610 A1 | 11/2003 | Lastovich et al. |
| 2003/0225373 A1 | 12/2003 | Bobroff et al. |
| 2003/0225374 A1 | 12/2003 | Mathiasen |
| 2003/0229308 A1 | 12/2003 | Tsals et al. |
| 2003/0229316 A1 | 12/2003 | Hwang et al. |
| 2004/0002682 A1 | 1/2004 | Kovelman et al. |
| 2004/0006316 A1 | 1/2004 | Patton |
| 2004/0044306 A1 | 3/2004 | Lynch et al. |
| 2004/0049159 A1 | 3/2004 | Barrus et al. |
| 2004/0055711 A1 | 3/2004 | Martin et al. |
| 2004/0059316 A1 | 3/2004 | Smedegaard |
| 2004/0068231 A1 | 4/2004 | Blondeau |
| 2004/0069044 A1 | 4/2004 | Lavi et al. |
| 2004/0087913 A1 | 5/2004 | Rogers et al. |
| 2004/0092865 A1 | 5/2004 | Flaherty et al. |
| 2004/0092875 A1 | 5/2004 | Kochamba |
| 2004/0111068 A1 | 6/2004 | Swenson |
| 2004/0112781 A1 | 6/2004 | Hofverberg et al. |
| 2004/0116865 A1 | 6/2004 | Bengtsson |
| 2004/0133164 A1 | 7/2004 | Funderburk et al. |
| 2004/0138612 A1 | 7/2004 | Shermer et al. |
| 2004/0138620 A1 | 7/2004 | Douglas et al. |
| 2004/0143216 A1 | 7/2004 | Douglas et al. |
| 2004/0143218 A1 | 7/2004 | Das |
| 2004/0158202 A1 | 8/2004 | Jensen |
| 2004/0158207 A1 | 8/2004 | Hunn et al. |
| 2004/0162518 A1 | 8/2004 | Connelly et al. |
| 2004/0162521 A1 | 8/2004 | Bengtsson |
| 2004/0171989 A1 | 9/2004 | Horner et al. |
| 2004/0178098 A1 | 9/2004 | Swenson et al. |

(56) References Cited

U.S. PATENT DOCUMENTS

| | | |
|---|---|---|
| 2004/0186446 A1 | 9/2004 | Ohshima |
| 2004/0193143 A1 | 9/2004 | Sauer |
| 2004/0199123 A1 | 10/2004 | Nielsen |
| 2004/0204673 A1 | 10/2004 | Flaherty et al. |
| 2004/0204687 A1 | 10/2004 | Mogensen et al. |
| 2004/0204690 A1 | 10/2004 | Yashiro et al. |
| 2004/0215151 A1 | 10/2004 | Marshall et al. |
| 2004/0220528 A1 | 11/2004 | Garcia, Jr. |
| 2004/0236284 A1 | 11/2004 | Hoste et al. |
| 2004/0238392 A1 | 12/2004 | Peterson et al. |
| 2004/0243065 A1 | 12/2004 | McConnell et al. |
| 2004/0254433 A1 | 12/2004 | Bandis et al. |
| 2004/0260235 A1 | 12/2004 | Douglas |
| 2004/0260250 A1 | 12/2004 | Harris et al. |
| 2005/0035014 A1 | 2/2005 | Cane |
| 2005/0038378 A1 | 2/2005 | Lastovich et al. |
| 2005/0043687 A1 | 2/2005 | Mogensen et al. |
| 2005/0049571 A1 | 3/2005 | Lastovich et al. |
| 2005/0065466 A1 | 3/2005 | Vedrine |
| 2005/0065472 A1 | 3/2005 | Cindrich et al. |
| 2005/0075606 A1 | 4/2005 | Botich et al. |
| 2005/0080386 A1 | 4/2005 | Reid |
| 2005/0101910 A1 | 5/2005 | Bowman et al. |
| 2005/0101912 A1 | 5/2005 | Faust et al. |
| 2005/0101932 A1 | 5/2005 | Cote et al. |
| 2005/0101933 A1 | 5/2005 | Marrs et al. |
| 2005/0107743 A1 | 5/2005 | Fangrow, Jr. |
| 2005/0113761 A1 | 5/2005 | Faust et al. |
| 2005/0119611 A1 | 6/2005 | Marano-Ford et al. |
| 2005/0119619 A1 | 6/2005 | Haining |
| 2005/0119637 A1 | 6/2005 | Lundgren et al. |
| 2005/0124936 A1 | 6/2005 | Mogensen et al. |
| 2005/0131347 A1 | 6/2005 | Marano-Ford et al. |
| 2005/0159709 A1 | 7/2005 | Wilkinson |
| 2005/0159714 A1 | 7/2005 | Gibson |
| 2005/0165382 A1 | 7/2005 | Fulford |
| 2005/0192560 A1 | 9/2005 | Walls et al. |
| 2005/0203461 A1 | 9/2005 | Flaherty et al. |
| 2005/0215979 A1 | 9/2005 | Kornerup et al. |
| 2005/0240154 A1 | 10/2005 | Mogensen et al. |
| 2005/0251098 A1 | 11/2005 | Wyss et al. |
| 2005/0256456 A1 | 11/2005 | Marano-Ford et al. |
| 2005/0261629 A1 | 11/2005 | Marano-Ford et al. |
| 2005/0277892 A1 | 12/2005 | Chen |
| 2005/0283114 A1 | 12/2005 | Bresina et al. |
| 2006/0015063 A1 | 1/2006 | Butikofer et al. |
| 2006/0015076 A1 | 1/2006 | Heinzerling et al. |
| 2006/0030815 A1 | 2/2006 | Csincsura et al. |
| 2006/0036214 A1 | 2/2006 | Mogensen et al. |
| 2006/0041224 A1 | 2/2006 | Jensen |
| 2006/0069351 A9 | 3/2006 | Safabash et al. |
| 2006/0069382 A1 | 3/2006 | Pedersen |
| 2006/0069383 A1 | 3/2006 | Bogaerts et al. |
| 2006/0095003 A1 | 5/2006 | Marano-Ford et al. |
| 2006/0095014 A1 | 5/2006 | Ethelfeld |
| 2006/0106346 A1 | 5/2006 | Sullivan et al. |
| 2006/0129123 A1 | 6/2006 | Wojcik |
| 2006/0135908 A1 | 6/2006 | Liniger et al. |
| 2006/0135913 A1 | 6/2006 | Ethelfeld |
| 2006/0142698 A1 | 6/2006 | Ethelfeld |
| 2006/0161108 A1 | 7/2006 | Mogensen et al. |
| 2006/0173410 A1 | 8/2006 | Moberg et al. |
| 2006/0173413 A1 | 8/2006 | Fan |
| 2006/0184104 A1 | 8/2006 | Cheney, II et al. |
| 2006/0184140 A1 | 8/2006 | Okiyama |
| 2006/0200073 A1 | 9/2006 | Radmer et al. |
| 2006/0241551 A1 | 10/2006 | Lynch et al. |
| 2006/0247553 A1 | 11/2006 | Diermann et al. |
| 2006/0247574 A1 | 11/2006 | Maule et al. |
| 2006/0253085 A1 | 11/2006 | Geismar et al. |
| 2006/0253086 A1 | 11/2006 | Moberg et al. |
| 2006/0264835 A1 | 11/2006 | Nielsen et al. |
| 2006/0264890 A1 | 11/2006 | Moberg et al. |
| 2007/0005017 A1 | 1/2007 | Alchas et al. |
| 2007/0016129 A1 | 1/2007 | Liniger et al. |
| 2007/0016159 A1 | 1/2007 | Sparholt et al. |
| 2007/0021729 A1 | 1/2007 | Mogensen et al. |
| 2007/0049865 A1 | 3/2007 | Radmer et al. |
| 2007/0049870 A1 | 3/2007 | Gray et al. |
| 2007/0051784 A1 | 3/2007 | Money et al. |
| 2007/0066955 A1 | 3/2007 | Sparholt et al. |
| 2007/0066958 A1 | 3/2007 | Wright |
| 2007/0088271 A1 | 4/2007 | Richards et al. |
| 2007/0093754 A1 | 4/2007 | Mogensen et al. |
| 2007/0104596 A1 | 5/2007 | Preuthun et al. |
| 2007/0112301 A1 | 5/2007 | Preuthun et al. |
| 2007/0112303 A1 | 5/2007 | Liniger |
| 2007/0129688 A1 | 6/2007 | Scheurer et al. |
| 2007/0129691 A1 | 6/2007 | Sage, Jr. et al. |
| 2007/0173767 A1 | 7/2007 | Lynch et al. |
| 2007/0179444 A1 | 8/2007 | Causey et al. |
| 2007/0185441 A1 | 8/2007 | Fangrow, Jr. |
| 2007/0191772 A1 | 8/2007 | Wojcik |
| 2007/0191773 A1 | 8/2007 | Wojcik |
| 2007/0203454 A1 | 8/2007 | Shermer et al. |
| 2007/0213673 A1 | 9/2007 | Douglas |
| 2007/0244448 A1 | 10/2007 | Lastovich et al. |
| 2007/0282269 A1 | 12/2007 | Carter et al. |
| 2007/0299409 A1 | 12/2007 | Whitbourne et al. |
| 2008/0058692 A1 | 3/2008 | Propp et al. |
| 2008/0119707 A1 | 5/2008 | Stafford |
| 2008/0200897 A1 | 8/2008 | Hoss et al. |
| 2008/0269687 A1 | 10/2008 | Chong et al. |
| 2008/0312601 A1 | 12/2008 | Cane' |
| 2008/0319416 A1* | 12/2008 | Yodfat ................ A61B 5/6849 604/513 |
| 2009/0062767 A1 | 3/2009 | Van Antwerp et al. |
| 2009/0118592 A1 | 5/2009 | Klitgaard |
| 2009/0326456 A1 | 12/2009 | Cross et al. |
| 2010/0004597 A1 | 1/2010 | Gyrn et al. |
| 2010/0022956 A1 | 1/2010 | Tipsmark et al. |
| 2010/0137829 A1 | 6/2010 | Nielsen et al. |
| 2010/0228226 A1* | 9/2010 | Nielsen ................ A61M 5/158 604/506 |
| 2010/0262078 A1 | 10/2010 | Blomquist |
| 2011/0054399 A1 | 3/2011 | Chong et al. |

FOREIGN PATENT DOCUMENTS

| | | |
|---|---|---|
| DE | 299 05 072 U1 | 9/1999 |
| DE | 101 17 285 A1 | 11/2002 |
| DE | 203 20 207 U1 | 11/2004 |
| EP | 0117632 B1 | 9/1984 |
| EP | 0239244 B1 | 2/1987 |
| EP | 0272530 A2 | 6/1988 |
| EP | 0451040 A1 | 10/1991 |
| EP | 0544837 B1 | 6/1993 |
| EP | 0615768 A2 | 9/1994 |
| EP | 0651662 B1 | 5/1995 |
| EP | 0652027 A1 | 5/1995 |
| EP | 0657184 A1 | 6/1995 |
| EP | 0688232 B1 | 12/1995 |
| EP | 0714631 B1 | 6/1996 |
| EP | 0744183 A2 | 11/1996 |
| EP | 0747006 A1 | 12/1996 |
| EP | 0775501 B1 | 5/1997 |
| EP | 0799626 A1 | 10/1997 |
| EP | 0937475 A2 | 8/1999 |
| EP | 0956879 A1 | 11/1999 |
| EP | 1086718 A1 | 3/2001 |
| EP | 1125593 A1 | 8/2001 |
| EP | 1329233 B1 | 7/2003 |
| EP | 1350537 A1 | 10/2003 |
| EP | 1360970 A1 | 11/2003 |
| EP | 1380315 A1 | 1/2004 |
| EP | 1407747 A1 | 4/2004 |
| EP | 1407793 A1 | 4/2004 |
| EP | 1421968 A2 | 5/2004 |
| EP | 1177802 B1 | 9/2004 |
| EP | 1475113 A1 | 11/2004 |
| EP | 1495775 A1 | 1/2005 |
| EP | 1502613 A1 | 2/2005 |
| EP | 1525873 A1 | 4/2005 |
| EP | 1527792 A1 | 5/2005 |

(56) References Cited

FOREIGN PATENT DOCUMENTS

| | | | |
|---|---|---|---|
| EP | 1559442 A2 | 8/2005 |
| EP | 1616594 A1 | 1/2006 |
| EP | 1704889 A1 | 9/2006 |
| EP | 1719537 A2 | 11/2006 |
| EP | 1762259 A1 | 3/2007 |
| EP | 1764125 A1 | 3/2007 |
| EP | 1776980 A1 | 4/2007 |
| EP | 1970091 A1 | 9/2008 |
| EP | 2272559 A1 | 1/2011 |
| FR | 2725902 A1 | 10/1994 |
| FR | 2 752 164 A1 | 2/1998 |
| GB | 906574 | 9/1962 |
| GB | 2 088 215 A | 6/1982 |
| GB | 2 230 702 A | 10/1990 |
| GB | 2 423 267 A | 8/2006 |
| GB | 2 450 872 A | 7/2007 |
| GB | 2 459 101 A | 10/2009 |
| JP | 10179734 A | 8/1991 |
| JP | 7051251 A | 11/1995 |
| JP | 8187286 A | 7/1996 |
| JP | 03-191965 A | 7/1998 |
| JP | 2002-028246 A | 1/2002 |
| RU | 2 238 111 C2 | 12/2003 |
| SU | 933 100 | 6/1982 |
| WO | WO 81/01795 A1 | 7/1981 |
| WO | WO 82/03558 A1 | 10/1982 |
| WO | WO 92/04062 A1 | 3/1992 |
| WO | WO 93/05840 A2 | 4/1993 |
| WO | WO 93/11709 A1 | 6/1993 |
| WO | WO 94/20160 A1 | 9/1994 |
| WO | WO 95/19194 A1 | 7/1995 |
| WO | WO 96/20021 A1 | 7/1996 |
| WO | WO 96/32981 A1 | 10/1996 |
| WO | WO 98/26835 A1 | 6/1998 |
| WO | WO 98/33549 A1 | 8/1998 |
| WO | WO 98/58693 A1 | 12/1998 |
| WO | WO 99/07435 A1 | 2/1999 |
| WO | WO 99/22789 A1 | 5/1999 |
| WO | WO 99/33504 A1 | 7/1999 |
| WO | WO 00/02614 A1 | 1/2000 |
| WO | WO 00/03757 A1 | 1/2000 |
| WO | WO 00/44324 A1 | 8/2000 |
| WO | WO 01/12746 A1 | 2/2001 |
| WO | WO 01/30419 A2 | 5/2001 |
| WO | WO 01/68180 A1 | 9/2001 |
| WO | WO 01/72353 A2 | 10/2001 |
| WO | WO 01/76684 A1 | 10/2001 |
| WO | WO 01/93926 A2 | 12/2001 |
| WO | WO 02/02165 A2 | 1/2002 |
| WO | WO 02/07804 A1 | 1/2002 |
| WO | WO 02/40083 A2 | 5/2002 |
| WO | WO 02/053220 A2 | 7/2002 |
| WO | WO 02/068014 A2 | 9/2002 |
| WO | WO 02/081012 A2 | 10/2002 |
| WO | WO 02/081013 A2 | 10/2002 |
| WO | WO 02/083206 A2 | 10/2002 |
| WO | WO 02/083228 A2 | 10/2002 |
| WO | WO 02/094352 A2 | 11/2002 |
| WO | WO 02/100457 A2 | 12/2002 |
| WO | WO 02/102442 A1 | 12/2002 |
| WO | WO 03/015860 A1 | 2/2003 |
| WO | WO 03/026728 A1 | 4/2003 |
| WO | WO 03/068305 A1 | 8/2003 |
| WO | WO 03/075980 A2 | 9/2003 |
| WO | WO 03/095003 A1 | 11/2003 |
| WO | WO 2004/012796 A1 | 2/2004 |
| WO | WO 2004/024219 A1 | 3/2004 |
| WO | WO 2004/026375 A1 | 4/2004 |
| WO | WO 2004/029457 A1 | 4/2004 |
| WO | WO 2004/030726 A1 | 4/2004 |
| WO | WO 2004/037325 A1 | 5/2004 |
| WO | WO 2004/054644 A1 | 7/2004 |
| WO | WO 2004/056412 A2 | 7/2004 |
| WO | WO 2004/064593 A2 | 8/2004 |
| WO | WO 2004/071308 A1 | 8/2004 |
| WO | WO 2004/087240 A1 | 10/2004 |
| WO | WO 2004/098683 A1 | 11/2004 |
| WO | WO 2004/101016 A1 | 11/2004 |
| WO | WO 2004/101071 A2 | 11/2004 |
| WO | WO 2004/110527 A1 | 12/2004 |
| WO | WO 2005/002649 A1 | 1/2005 |
| WO | WO 2005/004973 A1 | 1/2005 |
| WO | WO 2005/018703 A2 | 3/2005 |
| WO | WO 2005/037184 A2 | 4/2005 |
| WO | WO 2005/037350 A2 | 4/2005 |
| WO | WO 2005/039673 A2 | 5/2005 |
| WO | WO 2005/046780 A1 | 5/2005 |
| WO | WO 2005/065748 A1 | 7/2005 |
| WO | WO 2005/068006 A1 | 7/2005 |
| WO | WO 2005/072795 A2 | 8/2005 |
| WO | WO 2005/092410 A1 | 10/2005 |
| WO | WO 2005/094920 A1 | 10/2005 |
| WO | WO 2005/112800 A2 | 12/2005 |
| WO | WO 2005/118055 A1 | 12/2005 |
| WO | WO 2006/003130 A1 | 1/2006 |
| WO | WO 2006/015507 A2 | 2/2006 |
| WO | WO 2006/015600 A2 | 2/2006 |
| WO | WO 2006/024650 A2 | 3/2006 |
| WO | WO 2006/032689 A1 | 3/2006 |
| WO | WO 2006/032692 A1 | 3/2006 |
| WO | WO 2006/061027 A2 | 6/2006 |
| WO | WO 2006/061354 A1 | 6/2006 |
| WO | WO 2006/062680 A1 | 6/2006 |
| WO | WO 2006/062912 A1 | 6/2006 |
| WO | WO 2006/075016 A1 | 7/2006 |
| WO | WO 2006/077262 A1 | 7/2006 |
| WO | WO 2006/077263 A1 | 7/2006 |
| WO | WO 2006/089958 A1 | 8/2006 |
| WO | WO 2006/097111 A2 | 9/2006 |
| WO | WO 2006/108775 A2 | 10/2006 |
| WO | WO 2006/120253 A2 | 11/2006 |
| WO | WO 2006/121921 A2 | 11/2006 |
| WO | WO 2006/122048 A1 | 11/2006 |
| WO | WO 2007/000162 A2 | 1/2007 |
| WO | WO 2007/002523 A2 | 1/2007 |
| WO | WO 2007/020090 A1 | 2/2007 |
| WO | WO 2007/065944 A1 | 6/2007 |
| WO | WO 2007/071255 A1 | 6/2007 |
| WO | WO 2007/071258 A1 | 6/2007 |
| WO | WO 2007/093051 A1 | 8/2007 |
| WO | WO 2007/093182 A2 | 8/2007 |
| WO | WO 2007/122207 A1 | 11/2007 |
| WO | WO 2007/140631 A1 | 12/2007 |
| WO | WO 2007/140783 A2 | 12/2007 |
| WO | WO 2007/140785 A1 | 12/2007 |
| WO | WO 2007/141210 A1 | 12/2007 |
| WO | WO 2008/014791 A1 | 2/2008 |
| WO | WO 2008/014792 A1 | 2/2008 |
| WO | WO 2008/133702 A1 | 3/2008 |
| WO | WO 2008/048631 A1 | 4/2008 |
| WO | WO 2008/052545 A1 | 5/2008 |
| WO | WO 2008/065646 A1 | 6/2008 |
| WO | WO 2008/092782 A1 | 8/2008 |
| WO | WO 2008/092958 A2 | 8/2008 |
| WO | WO 2008/092959 A2 | 8/2008 |
| WO | WO 2008/135098 A1 | 11/2008 |
| WO | WO 2008/147600 A1 | 12/2008 |
| WO | WO 2008/148714 A1 | 12/2008 |
| WO | WO 2008/155145 A1 | 12/2008 |
| WO | WO 2008/155377 A1 | 12/2008 |
| WO | WO 2009/004026 A1 | 1/2009 |
| WO | WO 2009/007287 A1 | 1/2009 |
| WO | WO 2009/010396 A1 | 1/2009 |
| WO | WO 2009/010399 A1 | 1/2009 |
| WO | WO 2009/016635 A2 | 2/2009 |
| WO | WO 2009/033032 A1 | 3/2009 |
| WO | WO 2009/039013 A1 | 3/2009 |
| WO | WO 2009/098291 A1 | 8/2009 |
| WO | WO 2009/098306 A1 | 8/2009 |
| WO | WO 2009/101130 A1 | 8/2009 |
| WO | WO 2009/101145 A1 | 8/2009 |
| WO | WO 2009/103759 A1 | 8/2009 |
| WO | WO 2009/106517 A1 | 9/2009 |
| WO | WO 2009/144272 A1 | 12/2009 |

(56) References Cited

FOREIGN PATENT DOCUMENTS

| WO | WO 2010/003885 A1 | 1/2010 |
|----|-------------------|--------|
| WO | WO 2010/003886 A1 | 1/2010 |
| WO | WO 2010/030602 A1 | 3/2010 |
| WO | WO 2010/034830 A1 | 4/2010 |
| WO | WO 2010/072664 A1 | 7/2010 |
| WO | WO 2010/080715 A1 | 7/2010 |
| WO | WO 2010/112521 A1 | 10/2010 |
| WO | WO 2011/012465 A1 | 2/2011 |
| WO | WO 2011/015659 A1 | 2/2011 |
| WO | WO 2011/121023 A1 | 10/2011 |
| WO | WO 2012/041784 A1 | 4/2012 |
| WO | WO 2012/041923 A2 | 4/2012 |
| WO | WO 2012/045667 A2 | 4/2012 |
| WO | WO 2012/107440 A1 | 8/2012 |

OTHER PUBLICATIONS

"Why inset®?" inset® infusion set product overview; downloaded from the internet at http://web.archive.org/web/20040906102448/http://www.infusion-set.com/Default.asp?ID=108 on Jan. 1, 2008; two pages.

\* cited by examiner

INSERTION SYSTEM AND INSERTION KIT

This application claims the benefit under 35 U.S.C. §371 of International Application No. PCT/EP2011/066607, filed Sep. 23, 2011, which claims the benefit of U.S. Provisional Application Ser. No. 61/386,705, filed Sep. 27, 2010 and European Application No. 10179976.5, filed Sep. 27, 2010, which are incorporated by reference herein in their entirety.

The present invention relates to an insertion system, in particular for use with a base plate that during use is secured to the skin of a patient. More specifically, the present invention relates to an insertion system that can be operated both manually and with an inserter device.

Single use inserter devices for insertion of infusion sets having a base part with a cannula and an adhesive surface are well-known and enables a user to conveniently secure and insert the infusion set to the skin of a patient in one step. WO 2009/039013 discloses an insertion device for such infusion sets.

Recent developments have resulted in insertion systems comprising a base part and an inserter device having a cannula part to be mounted on the base part, when the base part has been secured to the skin of a patient by an adhesive surface of the base part.

Despite the developments, there is still a need for user-friendly insertion systems with a reduced material consumption.

SUMMARY

Accordingly, an insertion system is provided, the insertion system comprising a housing with a wall defining a cavity, an actuator element, a first part and a second part. The first part comprises a subcutaneous element and a first base element with at least one base plate engagement element. The second part comprises a needle hub and at least one insertion needle secured to the needle hub with the second part movably arranged from a first position to a second position relative to the housing along an insertion axis. The housing may comprise at least one first coupling element for releasably securing the insertion system to an inserter device, and the actuator element may comprise an outer part external to the housing such that manual actuation of the actuator element in relation to the housing is enabled.

It is an advantage of the insertion system that a user is able to manually insert a transcutaneous device, i.e. mount the transcutaneous device on a base plate and inserting a subcutaneous element without the use of a spring-loaded inserter device.

It is an advantage of the present insertion system that both manual and tool-assisted cannula insertion is enabled thereby allowing a user to choose between two different ways of insertion. Accordingly, the insertion system and insertion kit according to the invention provides improved user-flexibility. Furthermore, reuse of inserter devices are enabled leading to reduced material costs.

BRIEF DESCRIPTION OF THE DRAWINGS

The above and other features and advantages of the present invention will become readily apparent to those skilled in the art by the following detailed description of exemplary embodiments thereof with reference to the attached drawings, in which.

DETAILED DESCRIPTION

The figures are schematic and simplified for clarity, and they merely show details which are essential to the understanding of the invention, while other details have been left out. Throughout, the same reference numerals are used for identical or corresponding parts.

The housing of the insertion system comprises a wall defining a cavity. Further, the housing may comprise at least one first coupling element for releasably securing the insertion system to an inserter device. The at least one first coupling element of the housing may comprise a threaded portion on the inner or outer surface of the housing. The at least one first coupling element of the housing may comprise one or more recesses and/or protrusions configured to engage in releasable engagement with corresponding coupling element(s) of an inserter device. The at least one first coupling element of the housing may comprise one or more flexible arms with protrusion(s) and/or recess(es).

The housing may be a two-part housing comprising a first housing part and a second housing part, e.g. in order to facilitate assembly of the insertion system. The first housing part and the second housing part may be assembled by a snap fit lock, gluing, welding or other suitable means.

The insertion system comprises an actuator element that has an outer part that is external to the housing. Thereby manual actuation or manual movement of the actuator element in relation to the housing is enabled, allowing a user to insert and attach the first part both manually and by using an inserter device if desired or considered convenient by the user. The outer part of the actuator element may comprise an annular or partly annular member encircling the housing. The annular member may have a length (extension along insertion axis of at least or larger than 2 mm, such as in the range from 2 mm to 50 mm, e.g. in the range from 3 mm to 30 mm, in order to enable manual handling.

The outer part of the actuator element provides a gripping surface or grip element(s) for a person to facilitate manual and non-spring assisted insertion of the first part, e.g. by enabling manual movement of the actuator along the insertion axis to bring the first and second parts from the first to the second position. The outer part or grip element(s) of the actuator element may encircle or at least partly encircle the housing. The actuator element may comprise one or more arms projecting through and adapted to slide in one or more slits of the housing. The projecting arm(s) may each have or be connected to a grip element external to the housing, the grip element(s) enabling a person to grip and manually move the actuator along the insertion axis thereby inserting the first part. A grip element thus forms at least a part of the outer part. A grip element may be connected to one or a plurality of arms. The actuator element may comprise an inner part accommodated in the cavity of the housing.

The outer part of the actuator element may comprise one or more grip elements, e.g. a first grip element and/or a second grip element each encircling at least a part of the housing.

The actuator element may comprise one or more arms, e.g. including a first arm and/or a second arm connected to and extending from one or more grip elements, e.g. the first grip element. The first arm and/or the second arm may extend through at least one opening in the wall of the housing, e.g. the first arm may extend through a first opening formed as a slit in the wall of the housing parallel to the insertion axis and/or the second arm may extend through a second opening formed as a slit in the wall of the housing parallel to the insertion axis. The actuator element may comprise an inner part and at least a first arm connecting the inner part and the outer part, the first arm extending through a first opening in the wall of the housing. The inner part may be accommodated in the cavity.

The actuator element may engage with the second part such that the actuator element is configured to move the second part from the first position to the second position, e.g. in an insertion direction along the insertion axis. The actuator element may be secured to the second part such that moving the actuator element in both the insertion direction and in a retraction direction opposite the insertion direction cause moving the second part and vice versa. The second part and the actuator element may form a single unit, e.g. by molding the needle hub and the actuator element member in one piece.

The actuator element may be releasably secured to or engaged with the second part, e.g. the actuator element may be engaged or contacted with the second part in the first position and enable insertion of the second part and the first part in the insertion direction, i.e. move the second part to the second position. In the second position, the actuator element may be released from the second part, e.g. in order to allow moving the second part in the retraction direction independently of the actuator element.

Accordingly, the actuator element may comprise at least one engagement part for engaging the second part. The at least one engagement part may comprise one or more support surfaces configured to contact corresponding one or more support surfaces of the second part. The at least one engagement part of the actuator element may comprise one or more recesses and/or protrusions configured to engage corresponding engagement part(s) of the second part, e.g. in a snap fit lock or in releasable engagement. The at least one engagement part of the actuator element may comprise one or more flexible arms with protrusion(s) and/or recess(es). The actuator element may comprise one or more locking elements, e.g. configured to lock the actuator element to the housing in a position, e.g. one or more of the first position, the second position and a third position. The one or more locking elements of the actuator element may comprise one or more recesses and/or protrusions configured to engage corresponding locking parts of the housing. The inner part may form at least one engagement part for engaging the second part.

The insertion system, e.g. the housing, may comprise one or more release elements, e.g. configured to release or disengage different elements or parts of the insertion system during use. The release elements may comprise one or more recesses and/or one or more protrusions configured to disengage or release different elements or parts of the insertion system during use, e.g. configured to release the actuator element from the second part in the second position. Releasing the actuator element from the second part in the second position enables retraction of the second part with the needle independent of the manually operable actuator element. The release elements of the housing may be configured to cause a rotation of the actuator element in relation to the second part or vice versa about the insertion axis, e.g. when the second part is moved in the insertion direction and/or in retraction direction. Accordingly, the second part may in a first angular position about the insertion axis be engaged with the actuator element to provide movement of the second part with the actuator element in the insertion direction. In a second angular position about the insertion axis, the second part may be in a release position in relation to the actuator element, such that the second part can be moved in the retraction direction independently of the actuator element or the actuator element can be moved in the insertion direction without moving the second part. Such configuration with rotational release may obviate the use of flexible engagement elements between the actuator element and the second part.

The housing may comprise one or more locking elements. For example, the one or more locking elements may be configured to lock different elements of the insertion system in relation to the housing during use e.g. when elements are moved from one position to another and/or when elements are in selected positions. The locking elements may comprise one or more recesses and/or one or more protrusions configured to lock different elements or parts of the insertion system during use. The locking element(s) of the housing may be configured to lock the actuator element in relation to the housing in a position, e.g. the second position or a third position after retraction of the second part. The locking element(s) of the housing may be configured to lock the second part in relation to the housing in a position, e.g. the first or a third position after retraction of the second part in the retraction direction.

The wall of the housing may have one or more openings. The one or more openings may function as guiding member(s) or guideway for the actuator element and/or the second part during insertion. The one or more openings may provide access to the cavity from the outside of the housing, e.g. such that the outer part of the actuator may be connected to the second part through the one or more openings in the wall. The one or more openings may have any suitable shape, such as oblong, rectangular, optionally with rounded corners, curved, L-shaped, F-shaped. The one or more openings may comprise at least one slit extending substantially parallel to the insertion axis. The edge(s) of the wall forming the one or more openings may function as release elements for different parts of the insertion system.

Further, one or more guideways may be formed on the inner and/or outer surface of the housing for engagement with one or more guide protrusions or pins of the actuator element, and/or the second part. One or more guideways may be formed on the actuator element and/or the second part for engagement with one or more guide protrusions or pins on the inner or outer surface of the housing. Guide elements, such as guideways and guide protrusions may ensure correct orientation of different parts during insertion and/or function as release elements.

The insertion system comprises at least one first part. The insertion system may comprise a plurality of first parts, including a primary first part and a secondary first part. The first part comprises a subcutaneous element and a first base element, optionally defining a cavity and having at least one base plate engagement or locking element. The subcutaneous element may comprise one or more cannula elements and/or one or more sensor elements connected to one or more electrical connectors on the first base element. A cannula element and a sensor element may be incorporated in a single subcutaneous element. The first part may comprise one or more membranes. The first part may be configured for releasable engagement to the base plate.

The insertion system comprises at least one second part. The insertion system may comprise a plurality of second parts, including a primary second part and a secondary second part. The second part comprises a needle hub and at least one insertion needle secured to the needle hub. A part of the insertion needle extends inside a subcutaneous element, e.g. a cannula element and/or a sensor element, of the first part enabling insertion of the subcutaneous element (cannula element and/or the sensor element) under the skin of a user. The second part may be movably arranged relative to the housing along an insertion axis. The second part may be movably arranged from a first position (initial or retracted) to a second position (ejected). The second part may be locked in relation to the housing in selected positions, e.g. a third position.

During insertion into the skin and attachment to a base plate of a first part of the insertion system, it may be desirable to have a well-defined position of the insertion system in relation to the base plate, e.g. in order to avoid incorrect insertion of the first part. Accordingly, the insertion system, in particular the housing, may comprise at least one second coupling element for releasably securing or engaging the insertion system to a base plate. The at least one second coupling element may comprise a threaded portion, for example an inner or outer threaded portion on the housing wall. The at least one second coupling element of the housing may comprise one or more recesses and/or protrusions configured to engage in releasable engagement with corresponding coupling element(s) of base plate. The at least one second coupling element of the housing may comprise one or more flexible arms with protrusion(s) and/or recess(es).

The second coupling element may automatically be detached or released from base plate upon insertion of first part. A release element of the housing or of the base plate may be activated during use, e.g. by the first part reaching the second position. Thereby, the insertion system may be automatically released from the base plate when the first part has been inserted.

The base plate may be a an infusion port, a base plate in an infusion set, a patch system base plate (infusion and/or sensor), a base plate for a combination device (infusion and sensor), or a base plate for a subcutaneous sensor system.

The present invention allows a user to, manually or by using an inserter device (optionally spring-loaded and reusable), insert a first part of the insertion system into a base plate.

The insertion system may comprise a retraction mechanism configured to retract the second part of the insertion system upon insertion of the first part. The retraction mechanism may comprise at least one spring member. The spring member may be configured to move the second part from the second position back to the first position or to a third position, where the needle part is retracted from the skin and/or separated from the first part. The spring member may comprise a coil spring, e.g. a tension or compression coil spring.

The spring member may be made of metal or plastic, such as polyoxymethylene plastic (POM plastic) or other plastic material having suitable spring or elastic properties. A combination of metal and plastic may be employed. A plastic spring member may be preferred due to environmental and/or design considerations; however a metal spring member may be preferred due to material property considerations.

The spring member may comprise a spring element and a spring member base part, the spring member base part optionally including locking elements for locking the spring member to the housing and/or to the second part. The spring member may be pre-loaded in the first position. The spring member and the second part may form a single unit, e.g. by molding the needle hub and the spring member in one piece. The spring member, the actuator element, and the second part may form a single unit, e.g. by molding the spring member, the actuator element and the needle hub in one piece.

Also disclosed, is an insertion kit comprising an insertion system as disclosed herein and an inserter device comprising at least one coupling element for releasably securing the inserter device to the insertion system. The inserter device may comprise a spring element for spring-assisted insertion of the first part of the insertion system, when the inserter device is coupled to the insertion system. The insertion kit may as an alternative to the inserter device or in combination comprise a base plate having an adhesive surface, wherein the base plate comprises at least one locking element for locking or releasably engaging the first part of the insertion system to the base plate. The base plate may comprise coupling element(s) for engaging second coupling element(s) of the insertion system (housing) for releasably securing or engaging the insertion system to a base plate.

Figure 1:
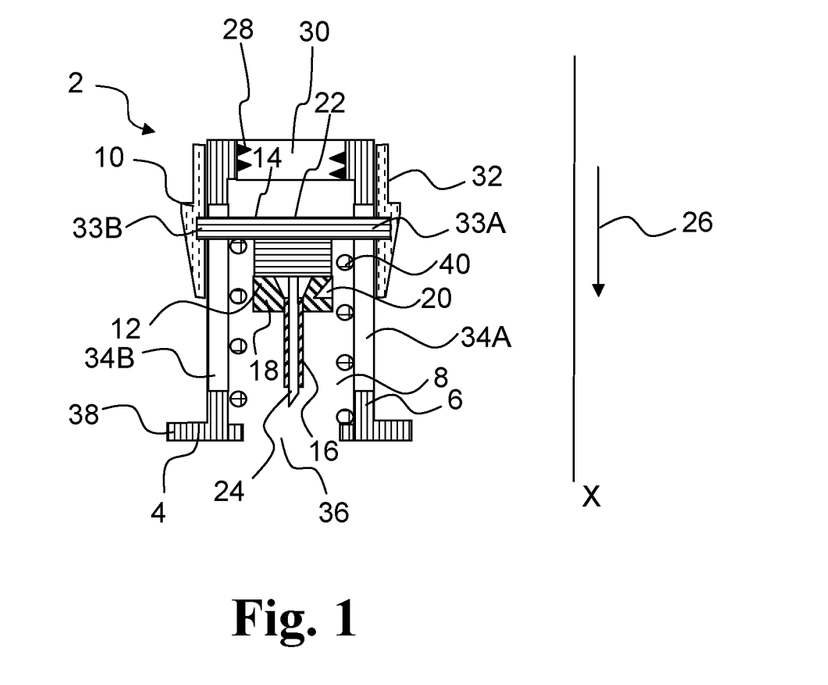
FIG. 1 schematically illustrates a cross section of an insertion system according to the invention.

FIG. 1 illustrates a cross sectional view of an insertion system according to the invention. The insertion system 2 comprises a housing 4 with at wall 6 defining a cavity 8. Further, the insertion system 2 comprises an actuator element 10, a first part 12 and a second part 14. The first part 12 comprises a subcutaneous element 16 with a cannula element, and a first base element 18 with at least one base plate engagement or locking element in form of recess 20. The second part 14 comprises a needle hub 22 and an insertion needle 24 secured to the needle hub with the second part 14 movably arranged from a first position (retracted or non-inserted position) as illustrated in FIG. 1 to a second position (ejected or inserted position) relative to the housing 4 in an insertion direction 26 along an insertion axis X. The housing 4 comprises at least one first coupling element 28 for releasably securing the insertion system to an inserter device (not shown). The at least one first coupling element 28 is formed as an inner thread in an opening 30 in the housing 4. The actuator element 10 comprises an outer part 32 external to the housing 4 such that manual actuation of the actuator element 10 is enabled. The outer part 32 as illustrated forms an annular member encircling the housing 4.

The needle hub 24 as illustrated in FIG. 1 comprises a first protruding element 33A extending through a first slit 34A in the wall 6 and a second protruding element 33B extending through a second slit 34B in the wall 6.

In the first position as illustrated in FIG. 1, the cavity 8 partly or fully accommodates the first part 12 and the second part 14. The housing 4 has at least one opening at a first end 36 allowing insertion of the first part 12 into the skin and base plate through the opening. The housing may comprise an opening at the second end 37, for example in order to facilitate coupling to an inserter device and/or insertion of the first part with an insertion rod of the inserter device. In the insertion system 2, the actuator element 10 and the second part 14 are secured to each other during assembly such that the actuator element 10 cannot move relative to the second part 14. The actuator element 10 and the second part 14 may constitute one member. Optionally, the housing 4 comprises at least one second coupling element 38 for releasably securing the insertion system to a base plate. The second coupling element 38 is formed by a protruding element, e.g. an annular flange member extending perpendicular to the insertion axis.

Optionally, the insertion system 2 comprises a retraction mechanism, e.g. as illustrated in FIG. 1, where the insertion system 2 comprises a spring member 40 supported in the housing and the second part such that the spring member 40 is loaded when the second part 14 is moved to the second position. The spring member 40 is configured to move or retract the second part 14 into the first position or to a third position where the second part is accommodated in the housing 4 after insertion of the first part.

Figure 2:
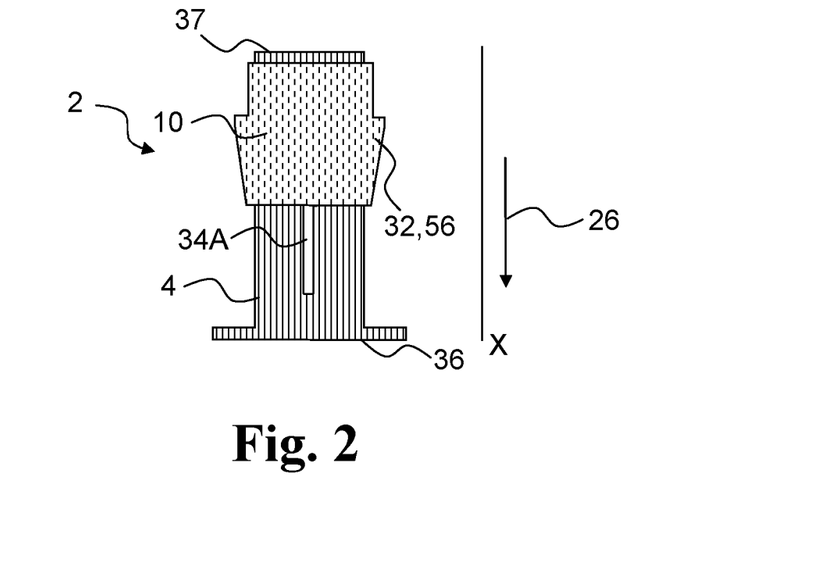
FIG. 2 is a side view of the insertion system of FIG. 1, FIG. 3 schematically illustrates a cross section of an insertion system according to the invention.

FIG. 2 is a side view of the insertion system 2 of FIG. 1. The first slit 34A and the second slit 34B (not shown) in the housing 4 extend parallel to the insertion axis X.

Figure 3:
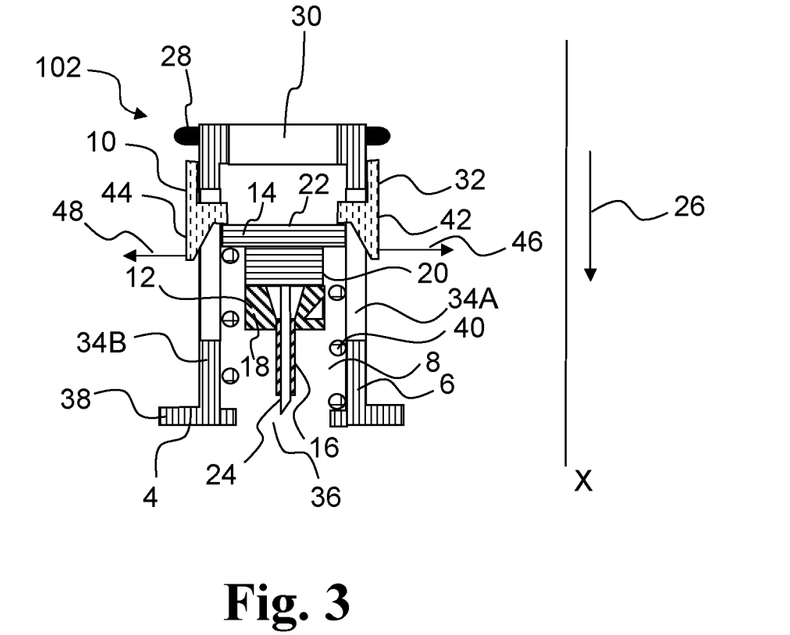

FIG. 3 illustrates a cross sectional view of an insertion system according to the invention. The insertion system 102 comprises an actuator element comprising a first engagement part 42 and a second engagement part 44 for engaging the second part 14. The engagement parts 42, 44 each comprise a flexible arm having a protrusion with a support surface configured to contact support surfaces of the second part in releasable engagement. In the first position as illustrated in FIG. 3, the engagement parts 42, 44 engage the second part such that during manual insertion, i.e. when the actuator element is moved in the insertion direction, the second part 14 moves with the actuator element 10, the actuator element pushing the second part in the insertion direction. In one or more embodiments, the actuator element may be configured to pull the second part in the insertion direction. When the second part 14 reaches the second position (first part inserted in base plate), the edges of the first and second slits 34A, 34B function as release elements by forcing the engagement elements 42, 44 radially outwards as indicated by arrows 46, 48, respectively, such that the second part 14 is released from the actuator element 10, thereby allowing the spring member 40, which has been loaded during insertion, to move the second part in the retraction direction back to the first position or to a third position if desired.

Figure 4:
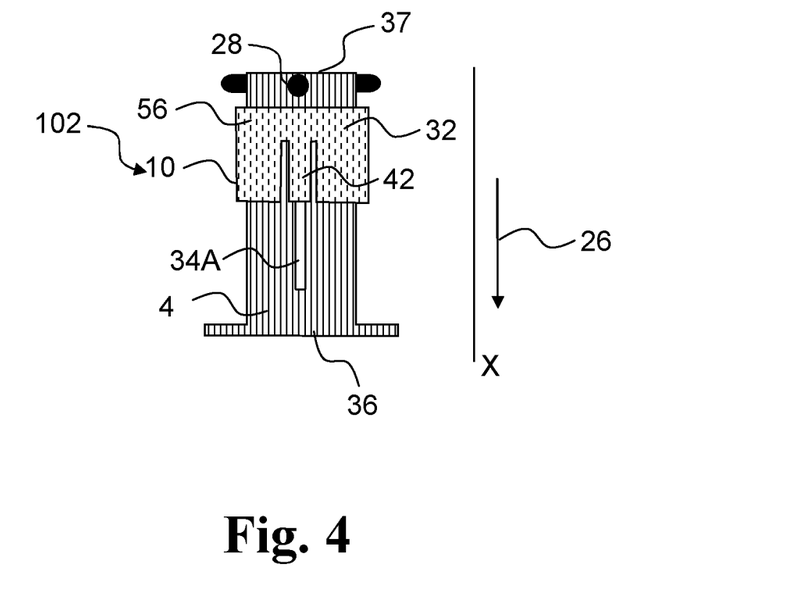
FIG. 4 is a side view of the insertion system of FIG. 3, FIG. 5 schematically illustrates a cross section of the insertion system of FIG. 3, FIG. 6 schematically illustrates a cross section of the insertion system of FIG. 3, FIG. 7 schematically illustrates a cross section of an insertion system according to the invention.

The housing 4 of insertion system 102 comprises at least one first coupling element 28 for releasably securing the insertion system to an inserter device (not shown). The at least one first coupling element 28 is formed as a plurality of outer protrusions, e.g two, three, four or more outer protrusions, extending radially away from the outer surface of the housing 4. The at least one first coupling element 28 illustrated in FIG. 3 and FIG. 4 comprise four outer protrusions distributed along the circumference of the housing 4.

Figure 5:
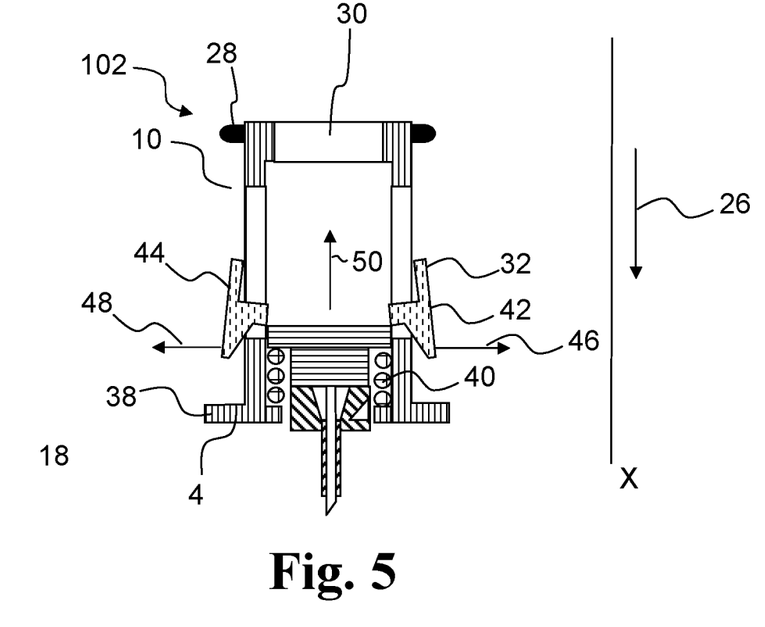

FIG. 5 illustrates the insertion system 102 with the first part and the second part in the second position. The first engagement part 42 and the second engagement part 44 of the actuator element are released or disengaged from the second part. The edges of the first slit and the second slit cause the first engagement part 42 and the second engagement part 44 to move radially outwards as indicated by arrows 46, 48 when the actuator element is moved in the insertion direction 26, thereby releasing the actuator element 10 from the second part 14. The release elements may be configured to move engagements elements in any suitable direction, such as radially inwards. Subsequently, the spring member 40, which has been loaded during insertion cause the second part 14 to be retracted in the retraction direction 50, e.g. back to the first position or to a third position. In the second position, the first part engages with the base plate and thus the second part is retracted into the housing functioning as a needle container.

Figure 6:
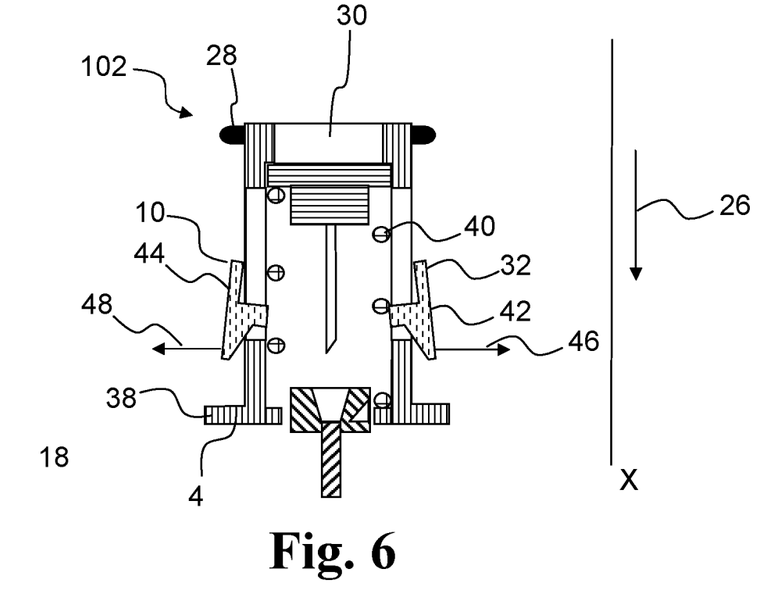

FIG. 6 illustrates the insertion system 102 with the second part 14 in a third position. In the third position, the actuator element cannot engage the second part 14, thereby ensuring that the needle can only be ejected manually from the housing once. By using an inserter device that is configured to move the second part independent from the actuator element, e.g. with a rod through the opening 30 allows a single manual ejection of the second part. An inserter device that is configured to insert the first part by moving the actuator element may ensure that the second part with the needle can only be ejected from the housing once thereby providing an insertion system and kit that is safe to use.

Figure 7:
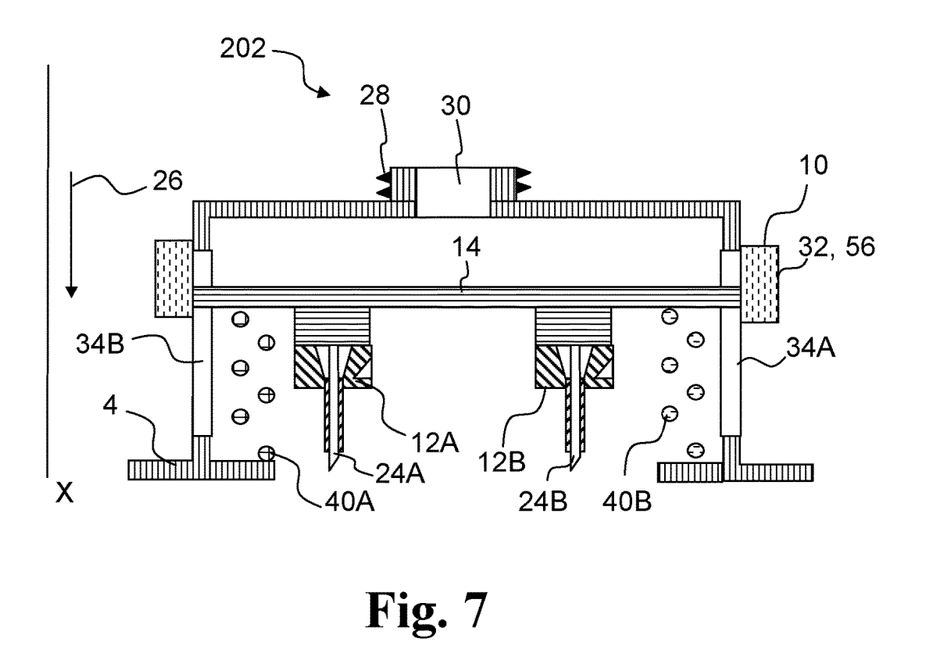

FIG. 7 schematically illustrates an insertion system 202 comprising a plurality of first parts including primary first part 12A and secondary first part 12B in the first position. The insertion system 202 further comprises a second part 14 comprising a first insertion needle 24A and a second insertion 24B configured for insertion of first parts 12A and 12B, respectively. One or more of the plurality of first parts optionally comprises a sensor element incorporated in the subcutaneous element 16. The actuator element 10 having an outer part 32 is fixed to the second part 14, however a release configuration between the actuator element and the second part, e.g. as illustrated in FIG. 3-6 may be employed. The insertion system 202 comprises a plurality of spring members including a first spring member 40A and a second spring member 40B. A single spring member may be employed.

Figure 8:
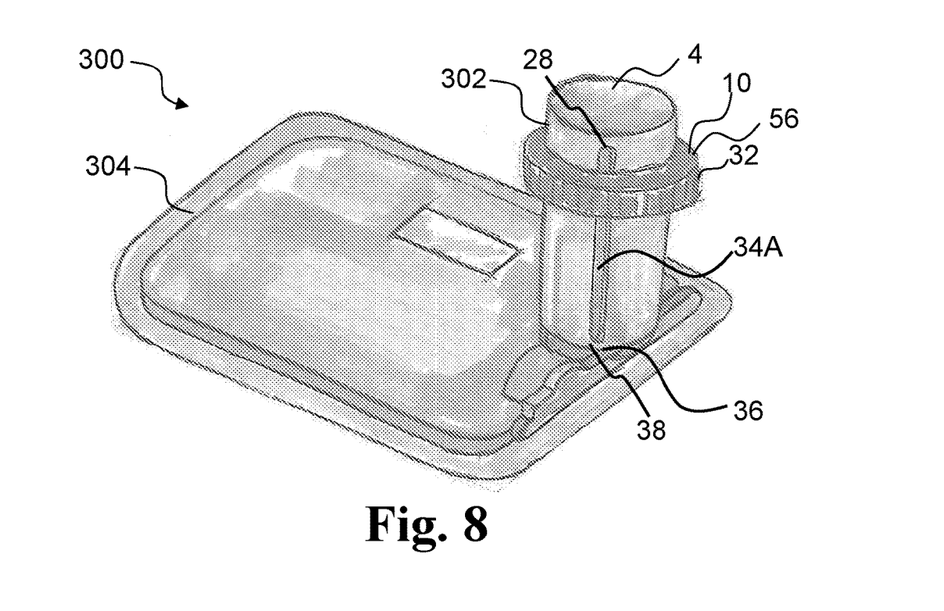
FIG. 8 is a perspective view of an insertion kit.

FIG. 8 is a perspective view of an insertion kit according to the invention. The insertion kit 300 comprises an insertion system 302 and a base plate 304. The insertion system 302 comprise first coupling elements 28 in the form of a first slit 34A and a second slit 34B enabling coupling elements of an inserter device to releasably couple to the insertion system. Further, the insertion system 302 at the first end 36 comprises second coupling elements 38 for coupling the insertion system corresponding coupling elements of the base plate 304.

Figure 9:
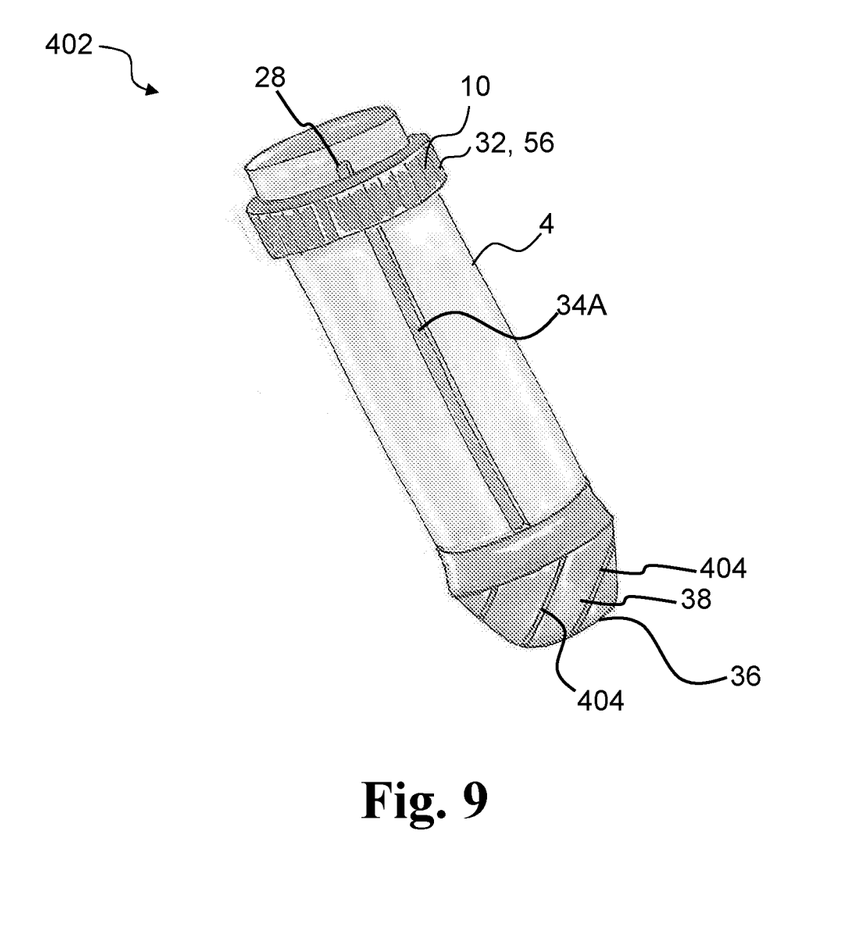
FIG. 9 is a perspective view of an insertion system.

FIG. 9 is a perspective view of an insertion system according to the invention. In the illustrated embodiment, the at least one second coupling element 38 is provided as one or more recesses and/or protrusions 404 in or on the outer surface of the housing, the recesses and/or protrusions 404 at least partly forming a threaded portion for coupling the insertion system 402 to a base plate. The housing 4 accommodates the first part and the second part (not shown).

Figure 10:
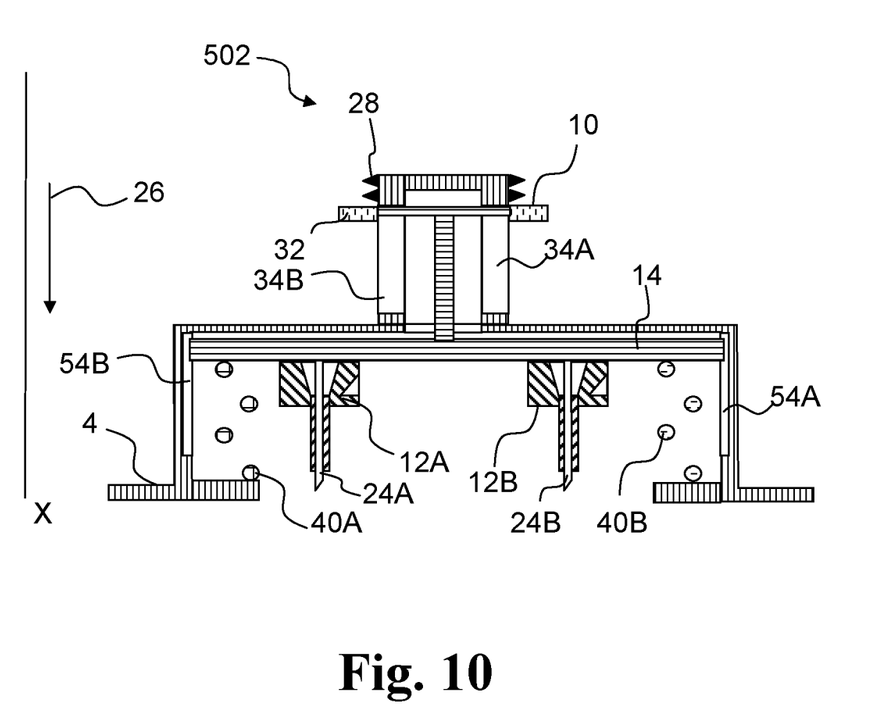
FIG. 10 is a perspective view of an insertion system.

FIG. 10 schematically illustrates an insertion system 402 comprising a plurality of first parts including primary first part 12A and secondary first part 12B in the first position. The insertion system 402 further comprises a second part 14 comprising a first insertion needle 24A and a second insertion 24B configured for insertion of first parts 12A and 12B, respectively. One or more of the plurality of first parts optionally comprises a sensor element incorporated in the subcutaneous element. The actuator element 10 having an outer part 32 is fixed to the second part 14, however a release configuration between the actuator element and the second part, e.g. as illustrated in FIG. 3-6 may be employed. The insertion system 402 comprises a plurality of spring members including a first spring member 40A and a second spring member 40B. A single spring member may be employed. A first guideway 54A and a second guideway 54B are formed in the inner surface of the housing 4 in order to guide the second part 14 during insertion.

Figure 11:
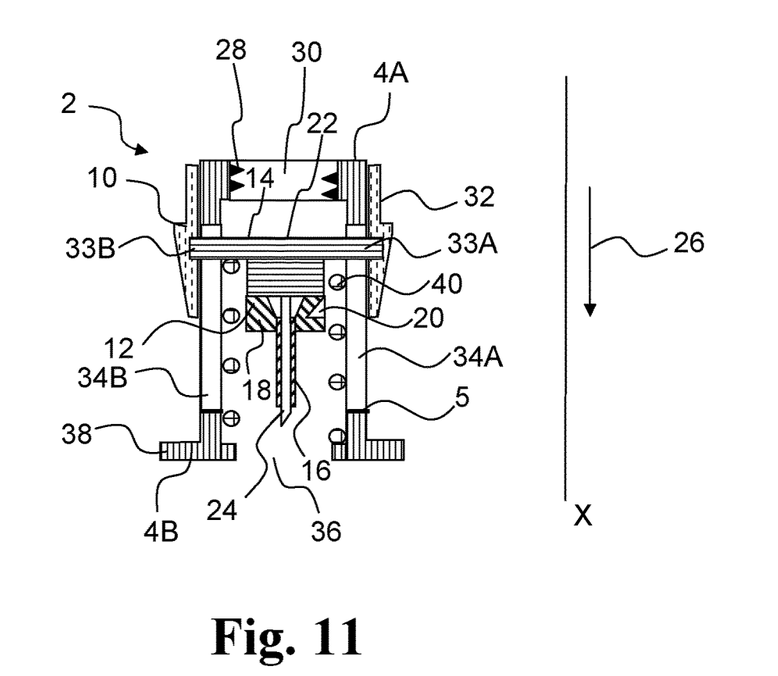
FIG. 11 is a perspective view of an insertion system with a two-part housing.

FIG. 11 shows the insertion system 2 comprising a two-part housing with a first housing part 4A and a second housing part 4B connected by a snap fit lock along interface 5.

Figures 12, 13:
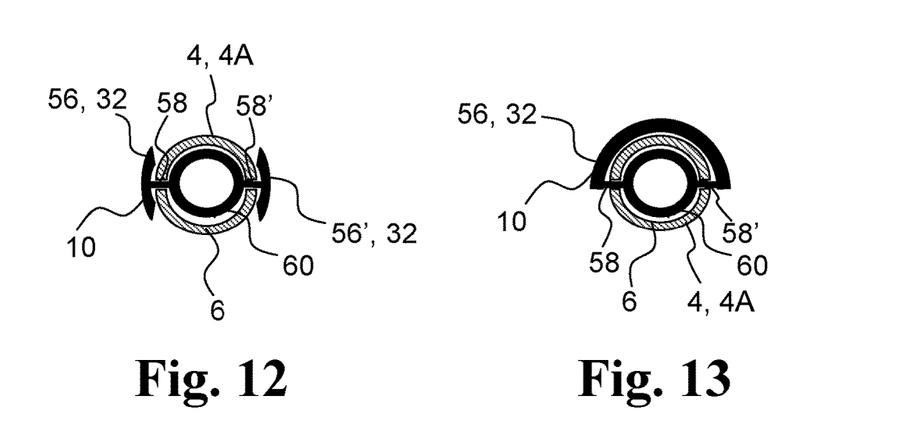
FIG. 12 shows an exemplary actuator and housing of an exemplary insertion device in a cross section perpendicular to the insertion axis.
FIG. 13 shows an exemplary actuator and housing of an exemplary insertion device in a cross section perpendicular to the insertion axis.

FIG. 12 and FIG. 13 show exemplary actuators and housings of exemplary insertion devices in cross sections perpendicular to the insertion axis. In FIG. 12, the insertion device comprises an actuator element 10 comprising an outer part 32 with a first grip element 56 and a second grip element 56' external to the housing 4. The first grip element 56 is connected to an inner part 60 of the actuator via a first arm 58 and the second grip element 56' is connected to the inner part 60 of the actuator via a second arm 58'. The first arm 58 and the second arm 56' extend through respective first and second slits in the housing wall 6. In FIG. 13, the insertion device comprises an actuator element with an outer part comprising a first grip element 56 external to the housing and connected to a first arm 58 and a second arm 58'. The first arm 58 and the second arm 56' extend through respective first and second slits in the housing wall 6 connecting the first grip element to the inner part 60 accommodated in the cavity.

It should be noted that in addition to the exemplary embodiments of the invention shown in the accompanying drawings, the invention may be embodied in different forms and should not be construed as limited to the embodiments set forth herein. Rather, these embodiments are provided so that this disclosure will be thorough and complete, and will fully convey the concept of the invention to those skilled in the art.

LIST OF REFERENCES 2, 102, 202, 302, 402, 502 Insertion system
4 Housing
4A First housing part
4B Second housing part
6 Wall
8 Cavity
10 Actuator element
12, 12A, 12B First part
14 Second part
16 Subcutaneous element
18 First base element
20 Base plate engagement element
22 Needle hub
24, 24A, 24B Insertion needle
26 Insertion direction
28 First coupling element
30 Opening
32 Outer part of actuator element
33A First protruding element
33B Second protruding element
34A First slit
34B Second slit
36 First end
37 Second end
38 Second coupling element
40, 40A, 40B Spring member
42 First engagement element
44 Second engagement element
46 Release direction
48 Release direction
50 Retraction direction
54A, 54B Guideway
56 First grip element
56' Second grip element
58 First arm
58' Second arm
60 Inner part of actuator element
X Insertion axis

The invention claimed is:

1. An insertion system for insertion into skin comprising:
a housing comprising a wall defining a cavity, and at least one first coupling element capable of releasably securing the insertion system to an inserter device,
a first part comprising a subcutaneous element and a first base element with at least one base plate engagement element,
a second part comprising a needle hub and at least one insertion needle secured to the needle hub, wherein the second part is moveable from a first position to a second position relative to the housing along an insertion axis;
an actuator element comprising an outer part external to the housing such that manual actuation of the actuator element in relation to the housing is enabled, wherein at least a part of the actuator element moves radially outward relative to the insertion axis when the second part is moved to the second position such that at least one insertion needle is inserted into the skin.

2. The insertion system according to claim 1, wherein the housing further comprises at least one second coupling element, wherein said at least one second coupling element releasably secures the insertion system to a base plate.

3. The insertion system according claim 1, wherein the actuator element engages with the second part such that the actuator element is configured to move the second part from the first position to the second position.

4. The insertion system according to claim 1, wherein the actuator element is released from the second part in the second position at least partly via the radially outward movement of the actuator element.

5. The insertion system according to claim 3, wherein the actuator element comprises at least one engagement part that engages the second part.

6. The insertion system according to claim 1, wherein the insertion system comprises a spring member configured to move the second part from the second position to the first position or a third position in a retraction direction.

7. The insertion system according to claim 1, wherein the outer part of the actuator element comprises an annular member encircling the housing.

8. The insertion system according to claim 1, wherein the housing wall has at least one slit parallel to the insertion axis.

9. The insertion system according to claim 1, comprising a plurality of first parts including a primary first part and a secondary first part.

10. The insertion system according to claim 1, wherein the outer part of the actuator element comprises a first grip element encircling at least a part of the housing.

11. The insertion system according to claim 10, wherein the actuator element comprises a first arm and second arm connected to and extending from the first grip element, the first arm and the second arm extending through at least one opening in the wall of the housing.

12. The insertion system according to claim 1, wherein the actuator element comprises an inner part and at least a first arm connecting the inner part and the outer part, the first arm extending through a first opening in the wall of the housing.

13. An insertion kit comprising an insertion system according to claim 1 and an inserter device comprising at least one coupling element, wherein said coupling element releasably secures the inserter device to the insertion system.

14. The insertion kit according to claim 13, comprising a base plate having an adhesive surface and comprising at least one cannula locking element, wherein said cannula locking element locks or engages the first part of the insertion system to the base plate.

15. An insertion kit comprising an insertion system according to claim 1 and a base plate having an adhesive surface and comprising at least one cannula locking element, wherein said cannula locking element locks and engages the first part of the insertion system to the base plate.

16. An insertion system for insertion into skin comprising:
a housing comprising a wall defining a cavity and at least one first coupling element for releasably securing the insertion system to an inserter device,
a first part comprising a subcutaneous element and a first base element with at least one base plate engagement element,
a second part comprising a needle hub and at least one insertion needle secured to the needle hub, wherein the second part is moveable from a first position to a second position relative to the housing along an insertion axis,
an actuator element comprising an outer part external to the housing such that manual actuation of the actuator element in relation to the housing is enabled, wherein at least a part of the actuator element moves radially outward relative to the insertion axis when the second part is moved to the second position, wherein when the insertion system is placed adjacent to skin, the at least one insertion needle is inserted into the skin.

17. The insertion system according to claim 16, wherein the housing comprises at least one second coupling element for releasably securing the insertion system to a base plate.

18. The insertion system according claim 16, wherein the actuator element engages with the second part such that the actuator element is configured to move the second part from the first position to the second position.

19. The insertion system according to claim 16, wherein the actuator element is released from the second part in the second position at least partly via the radially outward movement of the actuator element.

20. The insertion system according to claim 19, wherein the actuator element comprises at least one engagement part for engaging the second part.

21. The insertion system according to claim 16, wherein the insertion system comprises a spring member configured to move the second part from the second position to the first position or a third position in a retraction direction.

22. The insertion system according to claim 16, wherein the outer part of the actuator element comprises an annular member encircling the housing.

23. The insertion system according to claim 16, wherein the housing wall has at least one slit parallel to the insertion axis.

24. The insertion system according to claim 16, comprising a plurality of first parts including a primary first part and a secondary first part.

25. An insertion kit comprising an insertion system according to claim 16 and an inserter device comprising at least one coupling element for releasably securing the inserter device to the insertion system.

26. The insertion kit according to claim 25, comprising a base plate having an adhesive surface and comprising at least one cannula locking element for locking or engaging the first part of the insertion system to the base plate.

27. An insertion kit comprising an insertion system according to claim 16 and a base plate having an adhesive surface and comprising at least one cannula locking element for locking or engaging the first part of the insertion system to the base plate.

* * * * *